(12) United States Patent
Burtscher et al.

(10) Patent No.: US 9,532,930 B2
(45) Date of Patent: Jan. 3, 2017

(54) POLYMERIZABLE COMPOSITIONS WITH HIGH POLYMERIZATION DEPTH

(71) Applicant: Ivoclar Vivadent AG, Schaan (LI)

(72) Inventors: Peter Burtscher, Rankweil (AT); Norbert Moszner, Mauren (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 123 days.

(21) Appl. No.: 14/391,759

(22) PCT Filed: Apr. 11, 2013

(86) PCT No.: PCT/EP2013/057604
§ 371 (c)(1),
(2) Date: Oct. 10, 2014

(87) PCT Pub. No.: WO2013/153166
PCT Pub. Date: Oct. 17, 2013

(65) Prior Publication Data
US 2015/0080490 A1    Mar. 19, 2015

(30) Foreign Application Priority Data
Apr. 11, 2012   (EP) .................................... 12163823

(51) Int. Cl.
| | | |
|---|---|---|
| C08F 2/46 | (2006.01) | |
| C08F 2/50 | (2006.01) | |
| C08G 61/04 | (2006.01) | |
| A61K 6/083 | (2006.01) | |
| A61K 6/00 | (2006.01) | |

(52) U.S. Cl.
CPC ........... *A61K 6/0835* (2013.01); *A61K 6/0052* (2013.01)

(58) Field of Classification Search
CPC .......................... A61K 6/0835; A61K 6/0052
USPC ...................................... 522/18, 12, 1; 520/1
See application file for complete search history.

(56) References Cited

U.S. PATENT DOCUMENTS

| | | | |
|---|---|---|---|
| 6,043,361 A | 3/2000 | Evans et al. | |
| 6,344,556 B1 | 2/2002 | Evans et al. | |
| 2008/0277814 A1* | 11/2008 | Moszner ................. | A61K 6/083 264/19 |
| 2010/0249305 A1 | 9/2010 | Laubersheimer et al. | |
| 2011/0054066 A1 | 3/2011 | Moszner et al. | |
| 2011/0118380 A1* | 5/2011 | Moszner ............... | A61K 6/0017 523/116 |
| 2012/0010066 A1* | 1/2012 | Fischer ................. | A61K 6/0215 501/32 |
| 2012/0010322 A1 | 1/2012 | Moszner et al. | |

FOREIGN PATENT DOCUMENTS

| | | |
|---|---|---|
| DE | 3801511 A1 | 7/1989 |
| DE | 19616183 A1 | 9/1997 |
| DE | 19903177 A1 | 7/2000 |
| EP | 0184095 A2 | 11/1985 |
| EP | 1413569 A1 | 4/2004 |
| EP | 1905413 A1 | 4/2008 |
| EP | 2233449 A1 | 9/2010 |

OTHER PUBLICATIONS

Ilie, N., et al., Investigations on mechanical behaviour of dental composites, Clin. Oral Invest, Feb. 26, 2009, vol. 13, pp. 427-438.
Rueggeberg, F., State-of-the-art: Dental photocuring—A Review, Dental Materials, vol. 27, Jan. 2011, pp. 39-52.
Moszner, R., et al., 8. Photoinitiators for direct adhesive restorative materials, Basics and Application of Photopolymerization Reactions, vol. 1, 2010, pp. 91-112.
Lee, J.H., et al., Cure depth in photopolymerization: Experiments and theory, J. Mater. Res., vol. 16, No. 12, Dec. 2001, pp. 3536-3544.
Mahn, E., Klinische Kriterien fur die erfolgreiche Komposite-Aushartung, Zahnmedizin, 2011, pp. 50-59.
Bluephase brochure, Ivoclar Vivadent AG, 2008, pp. 1-8.
Rueggeberg, F., Determination of resin cure using infrared analysis without an internal standard, Dent. Mater., Jul. 1994, vol. 10, pp. 282-286.
Watts, D.C., et al., Characteristics of Visible-light-activated Composite Systems, Br. Dent. J., Mar. 24, 1984, vol. 156, pp. 209-215.

\* cited by examiner

Primary Examiner — Ling Choi
Assistant Examiner — Jessica E Whiteley
(74) Attorney, Agent, or Firm — Ann M. Knab; Thad McMurray

(57) ABSTRACT

The invention relates to a composition with at least one polymerizable binder, wherein the composition contains a photoinitiator mixture which contains (a) at least one diacylgermanium compound of general formula (I)

Formula (I)

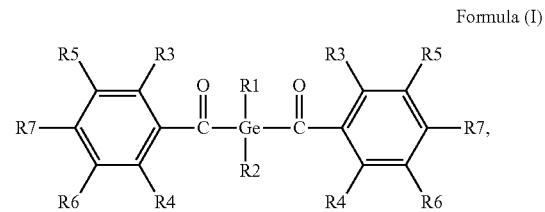

in which $R^1$, $R^2$ independently of each other are a linear $C_{1-4}$-alkyl, or $C_{2-4}$-alkenyl radical, which can be substituted by one or more polymerizable groups; $R^3$, $R^4$ independently of each other are in each case H, halogen, a branched or linear $C_{1-4}$-alkyl or —O—$C_{1-4}$-alkyl radical; $R^5$, $R^6$, $R^7$ independently of each other are in each case H, halogen, a linear $C_{1-20}$-alkyl, -alkenyl, -alkoxy or -alkenoxy radical, which can be interrupted by one or more —O—, —S— or —$NR^8$— radicals and substituted by one or more polymerizable groups; and $R^8$ independently is in each case H, a $C_{1-20}$-alkyl, -alkenyl, -alkoxy or -alkenoxy radical, (b) at least one α-diketone and (c) at least one accelerator, as well as the use of the composition for example for producing a filling composite.

17 Claims, No Drawings

POLYMERIZABLE COMPOSITIONS WITH HIGH POLYMERIZATION DEPTH

CROSS-REFERENCE TO RELATED APPLICATIONS

This application is a National Stage application of International patent application PCT/EP2013/057604 filed on Apr. 11, 2013, which claims priority to European patent application No. 12163823.3 filed on Apr. 11, 2012, the disclosures of which are incorporated herein by reference in their entirety.

The present invention relates to polymerizable compositions comprising a photoinitiator mixture that contains, in addition to an α-diketone and an accelerator, at least one diacylgermanium compound. The compositions are particularly suitable for the preparation of dental adhesives, cements and filling composites.

Light-curing composite restorations have achieved a very dominant position today in dental filling therapy (cf. N. Ilie, R. Hickel, Clin. Oral Invest. 13 (2009) 427-438). The curing of the composites is usually carried out by irradiation with blue light in the wavelength range of approx. 400-500 nm using different radiation sources, primarily halogen lamps or LEDs (light emitting diodes), but also argon ion lasers or plasma arc devices (cf. F. Rueggeberg, Dental Materials 27 (2011) 39-52). The filling composites are largely based on filled dimethacrylate resins which can contain a mixture of camphorquinone (CQ) and an amine accelerator as a photoinitiator system (N. Moszner, R. Liska: Photoinitiators for direct adhesive restorative materials, in Basics and Application of Photopolymerization Reactions, Vol. 1, Eds.: J. P. Fourassier, X. Allonas, Research Signpost, Kerala 2010, 91-112).

For the clinical performance of the filling composites, a good depth of cure is of central importance. According to ISO 4049-2009 ("Dentistry—Polymer-based restorative materials") the depth of cure is determined such that a cylindrical composite test piece is irradiated in a steel mould for the recommended time. The test piece is then taken out of the mould and the non-polymerized composite is removed with a plastic spatula. The height of the remaining cylinder, divided by 2, is defined as the depth of cure and is effectively a measure for how efficiently the composite can be cured by the irradiated light.

The depth of cure is dependent both on the process parameters and on the material properties. There is thus a logarithmic correlation e.g. between depth of cure and the intensity of the irradiated light and the exposure time respectively (cf. J. H. Lee, R. K. Prud'homme, I. A. Aksay, J. Mater. Res. 16 (2001) 3536-3544). The emission spectrum of the radiation source should match well with the absorption spectrum of the photoinitiator. Furthermore, the depth of cure correlates with the translucence of the composite, which in turn is influenced by, among other things, the refractive index of the resin matrix and the fillers, by the size of the filler particles as well as the type and concentration of the dyes added (E. Mahn, Zahnmedizin 2011, 50-59). The depth of cure is furthermore influenced by the type and concentration of the photoinitiator system, wherein monomolecular photoinitiators are easier to control than bimolecular photoinitiator systems. Examples of monomolecular photoinitiators are the commercially available compounds 2,4,6-trimethylbenzoyl diphenylphosphine oxide ($\lambda_{max}$=365 nm) and bis(2,4,6-trimethylbenzoyl)phenylphosphine oxide ($\lambda_{max}$=397 nm). These compounds can be used alone or combined with other photoinitiators to achieve a faster polymerization of the resin matrix or a curing in two steps (cf. EP 184 095 B1, DE 38 01 511 A1). The use of acylgermanes, which can be used as monomolecular photoinitiators in the visible range and which are characterized by a high through-curing depth, is disclosed in EP 1 905 413 A1.

The object of the invention is to provide polymerization initiator systems which can be activated with visible light and which result in an improved through-curing depth of the material to be cured. In particular, polymerizable compositions are to be provided which are suitable as composites for dental applications and which are characterized by an improved depth of cure, very good bleaching behaviour, relatively fast curing and very good mechanical properties of the cured material, even in deeper layers.

According to the invention, this object is achieved by compositions with at least one polymerizable binder, wherein the compositions have a photoinitiator mixture which contains
(a) at least one diacylgermanium compound of Formula (I),
(b) at least one α-diketone and
(c) at least one accelerator Formula (I)

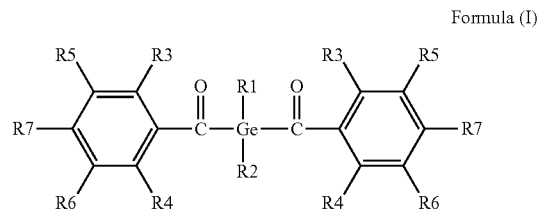

wherein
$R^1$, $R^2$ independently of each other are a $C_{1-4}$-alkyl or $C_{2-4}$-alkenyl radical which can be substituted by one or more polymerizable groups;
$R^3$, $R^4$ independently of each other are in each case H, halogen, a branched or linear $C_{1-4}$-alkyl or —O—$C_{1-4}$-alkyl radical;
$R_5$, $R^6$ independently of each other are in each case H, halogen, a linear $C_{1-20}$-alkyl, -alkenyl, -alkoxy or -alkenoxy radical which can be interrupted by one or more —O—, —S— or —$NR^8$— radicals and substituted by one or more polymerizable groups;
$R^7$ independently of each other is in each case H, halogen, a linear $C_{1-20}$-alkyl, -alkenyl, -alkoxy or -alkenoxy radical which can be interrupted by one or more —O—, —S— or —$NR^8$— radicals and substituted by one or more polymerizable groups; and
$R^8$ independently is in each case H, a $C_{1-20}$-alkyl, -alkenyl, -alkoxy or -alkenoxy radical.

Surprisingly, it was found that the use of a combination according to the invention of photoinitiators during the irradiation of polymerizable binders with light, preferably in the visible range, in particular with a wavelength of from 380 to 500 nm, leads to an improved depth of cure and to very good mechanical properties even in deeper layers of the material to be cured compared with conventional photoinitiators. The term "photoinitiator" is to refer here to substances and substance mixtures which form radicals upon irradiation with light and can thus trigger a polymerization of the polymerizable binder or accelerate such a polymerization, and is to include in particular monomolecular and bimolecular photoinitiators.

The photoinitiator mixture of the composition according to the invention can preferably contain, in addition to the components (a) to (c), at least one acyl or bisacyl phosphine oxide.

In a preferred embodiment, the photoinitiator mixture of the composition according to the invention contains, relative to the mass of the polymerizable binder,
(a) 0.05 to 1.1 wt.-% diacylgermanium compound,
(b) 0.1 to 1.1 wt.-% α-diketone,
(c) 0.1 to 2.1 wt.-% accelerator, in particular amine accelerator and
(d) 0 to 2.1 wt.-% acyl- or bisacyl phosphine oxide.

In a further preferred embodiment, the photoinitiator mixture contains, relative to the mass of the polymerizable binder,
(a) 0.1 to 0.5 wt.-% diacylgermanium compound,
(b) 0.2 to 0.6 wt.-% α-diketone,
(c) 0.3 to 1.5 wt.-% accelerator, in particular amine accelerator and
(d) 0 to 1.5 wt.-% acyl or bisacyl phosphine oxide.

Particularly preferably, the photoinitiator mixture of the composition contains, relative to the mass of the polymerizable binder,
(a) 0.2 to 0.5 wt.-% diacylgermanium compound,
(b) 0.2 to 0.5 wt.-% α-diketone,
(c) 0.4 to 0.8 wt.-% accelerator, in particular amine accelerator and
(d) 0.1 to 0.6 wt.-% acyl or bisacyl phosphine oxide.

The photoinitiator mixture of the composition contains, in addition to one or more α-diketones and one or more accelerators, at least one specific diacylgermanium compound of Formula (I). All stereoisomeric forms and mixtures of various stereoisomeric forms such as e.g. racemates are encompassed by Formula (I) and the other formulae shown here. The formulae cover only those compounds that are compatible with the chemical valence theory. The indication that a radical can be interrupted by a hetero atom such as O is to be understood to mean that the O atoms are inserted into the carbon chain of the radical, i.e. are bordered on both sides by carbon atoms. The number of O atoms is therefore smaller than the number of carbon atoms by at least 1 and the O atoms cannot be terminal. According to the invention, radicals that are not interrupted by O atoms are preferred. Halogen (abbreviated to hal) preferably stands for F, Cl, Br or I, in particular F, Cl, quite particularly preferably Cl. Preferred polymerizable groups which can be present as substituents in the above radicals are vinyl, styryl, (meth)acrylate, (meth)acrylamide and/or N-alkylacrylamide, particularly preferably (meth)acrylate, (meth)acrylamide and/or N-alkylacrylamide.

According to invention, those compositions that contain a diacylgermanium compound of Formula (II) as constituent (a) are preferred:

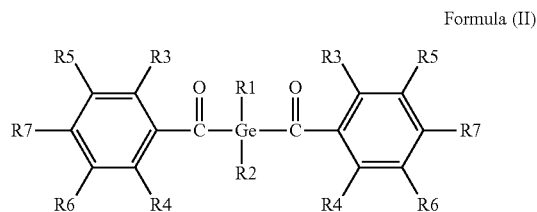

Formula (II)

wherein
$R^1$, $R^2$ independently of each other are a linear $C_{1-4}$-alkyl radical;
$R^3$, $R^4$ are in each case H;
$R^5$, $R^6$ are in each case H; and $R^7$ independently of each other is in each case H, a linear $C_{1-6}$-alkyl or -alkoxy radical, preferably independently of each other is in each case H or a $C_{1-6}$-alkoxy radical.

Particularly preferably, the diacylgermanium compound (a) is selected from the group consisting of bis(4-methoxybenzoyl)diethylgermanium, dibenzoyl diethylgermanium and mixtures thereof. Quite particularly preferably, the composition contains bis(4-methoxybenzoyl)diethylgermanium as diacylgermanium compound (a). 9,10-phenanthrenequinone, 1-phenylpropane-1,2-dione, diacetyl, 4,4'-dichlorobenzil, camphorquinone or their derivatives can preferably be used as α-diketones. In particular, the photoinitiator mixture contains an α-diketone which is selected from the group consisting of camphorquinone, 1-phenylpropane-1,2-dione and mixtures thereof.

Amine accelerators and/or amine-free accelerators are suitable as accelerators. It is particularly preferred that the composition according to the invention contains at least one amine accelerator as accelerator (c).

Tertiary amines can be used as amine accelerators, such as e.g. tertiary aromatic amines such as N,N-dialkylanilines, -p-toluidines or -3,5-xylidines, p-(N,N-dialkylamino)phenyl-ethanol, -benzoic acid derivatives, -benzaldehydes, -phenylacetic acid esters or -phenylpropionic acid esters. Specific examples for this are N,N-dimethylaniline, N,N-dimethyl-p-toluidine, N,N-3,5-tetramethylaniline, N,N-dimethylamino-p-benzaldehyde, p-(dimethylamino)benzoic acid ethyl ester or p-(dimethyl-amino)benzonitrile. Also suitable are tertiary aliphatic amines, such as e.g. tri-n-butylamine, dimethylaminoethan-2-ol, triethanolamine, dimethylaminoethyl methacrylate, N,N-dimethylbenzylamine, or heterocyclic amines, such as e.g. 1,2,2,6,6-pentamethylpiperidine, or amino acid derivatives, such as e.g. N-phenylglycine. The amine accelerator is preferably selected from the group consisting of p-(dimethylamino)benzoic acid ethyl ester, dimethylaminoethyl methacrylate, N,N-dimethylaniline, N,N-dimethyl-p-toluidine, triethanolamine and mixtures thereof.

Compositions containing acid monomers as binders, such as e.g. self-adhesive composites, can also contain, in addition to or instead of amine accelerators, amine-free accelerators, such as e.g. sulphinic acids or sulphinates, borates, enolates, phosphines or other compounds containing active hydrogen atoms, such as heterocyclic compounds, e.g. morpholine derivatives or 1,3-dioxolanes.

Suitable acyl or bisacyl phosphine oxides are listed in, among others, EP 0 007 508, EP 0 073 413 A2 (p. 2, l. 27 to p. 3, l. 14; p. 3, ll. 1-13), EP 0 184 095 A2 (p. 2, l. 4 to p. 3, l. 19; p. 4, l. 34 to p. 5, l. 26) and EP 0 615 980 A2 (in particular p. 2, ll. 21-35; p. 3, l 57 to p. 5, l. 28). Specific examples are the commercially available compounds 2,4,6-trimethylbenzoyl diphenylphosphine oxide (Lucirin® TPO, BASF) and bis(2,4,6-trimethylbenzoyl)phenylphosphine oxide (Irgacure® 819, Ciba). The photoinitiator mixture of the composition according to the invention can thus contain, according to one embodiment, an acyl or bisacyl phosphine oxide selected from the group consisting of 2,4,6-trimethylbenzoyl diphenylphosphine oxide, bis(2,4,6-trimethylbenzoyl)phenylphosphine oxide and mixtures thereof. The photoinitiator mixture preferably contains a bisacyl phosphine oxide and particularly preferably bis(2,4,6-trimethylbenzoyl)phenylphosphine oxide.

The compositions according to the invention preferably also contain, in addition to the photoinitiator mixture, a polymerizable binder. Binders based on radically polymerizable monomers and/or prepolymers are preferred.

Mono- or multifunctional (meth)acrylates or mixtures thereof are particularly suitable as radically polymerizable binders. By monofunctional (meth)acrylic compounds are meant compounds with one, by multifunctional (meth) acrylic compounds are meant compounds with two or more, preferably 2 to 3, polymerizable groups. Suitable examples are methyl, ethyl, 2-hydroxyethyl, butyl, benzyl, tetrahydrofurfuryl or isobornyl (meth)acrylate, p-cumyl-phenoxyethylene glycol methacrylate (CMP-1E), bisphenol-A-di(meth) acrylate, bis-GMA (an addition product of methacrylic acid and bisphenol-A-diglycidyl ether), ethoxy- or propoxylated bisphenol-A-dimethacrylate, such as e.g. the bisphenol-A-dimethacrylate SR-348c (Sartomer) with 3 ethoxy groups or 2,2-bis[4-(2-methacryloxy propoxy)phenyl]propane, UDMA (an addition product of 2-hydroxyethyl methacrylate and 2,2,4-trimethyl-hexamethylene diisocyanate), di-, tri- or tetraethylene glycol di(meth)acrylate, trimethylolpropane tri (meth)acrylate, pentaerythritol tetra(meth)acrylate, as well as glycerin di- and trimethacrylate, 1,4-butanediol di(meth) acrylate, 1,10-decanediol di(meth)acrylate ($D_3MA$) or 1,12-dodecanediol di(meth)acrylate. Preferred (meth)acrylate monomers are benzyl, tetrahydrofurfuryl or isobornyl methacrylate, p-cumyl-phenoxyethylene glycol methacrylate, 2,2-bis[4-(2-methacryloxy propoxy)phenyl]propane, bis-GMA, UDMA, SR-348c and $D_3MA$.

N-mono- or N-disubstituted acrylamides, such as e.g. N-ethylacrylamide or N,N-dimethacrylamide, or bisacrylamides, such as e.g. N,N'-diethyl-1,3-bis(acrylamido)propane, 1,3-bis(methacrylamido)propane, 1,4-bis(acrylamido) butane or 1,4-bis(acryloyl)piperazine can also be used as radically polymerizable binders.

Furthermore, known low-shrinkage radically ring-opening polymerizable monomers, such as e.g. mono- or multifunctional vinylcyclopropanes or bicyclic cyclopropane derivatives (cf. DE 196 16 183 C2 or EP 03 022 855) or cyclic allyl sulphides (cf. U.S. Pat. No. 6,043,361 and U.S. Pat. No. 6,344,556) can also be used as radically polymerizable binders, which can in addition also be used in combination with the above-listed di(meth)acrylate crosslinkers.

Moreover, radically polymerizable polysiloxanes which can be produced from suitable methacryl silanes such as e.g. 3-(methacryloyloxy)propyltrimethoxysilane and are described e.g. in DE 199 03 177 C2 can be used as radically polymerizable binders.

Mixtures of the previously named monomers with further radically polymerizable, acid-group-containing adhesive monomers can also be used for self-adhesive composites as radically polymerizable binders. Suitable acid-group-containing monomers are polymerizable carboxylic acids, such as maleic acid, acrylic acid, methacrylic acid, 2-(hydroxymethyl)acrylic acid, 4-(meth)acryloyloxyethyltrimellitic acid anhydride, 10-methacryloyloxydecylmalonic acid, N-(2-hydroxy-3-methacryloyloxypropyl)-N-phenylglycine and 4-vinylbenzoic acid. Examples of suitable phosphonic acid monomers are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl-phosphonic acid, 2-[4-(dihydroxyphosphoryl)-2-oxa-butyl] acrylic acid or 2-[4-(dihydroxyphosphoryl)-2-oxa-butyl] acrylic acid ethyl ester or -2,4,6-trimethylphenyl ester. Examples of suitable acidic polymerizable phosphoric acid esters are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol pentamethacryloyloxy phosphate, 10-methacryloyloxydecyl dihydrogen phosphate, phosphoric acid mono-(1-acryloyl-piperidin-4-yl)ester, 6-(methacrylamido)hexyl dihydrogen phosphate and 1,3-bis-(N-acryloyl-N-propyl-amino)-propan-2-yl dihydrogen phosphate. Examples of suitable polymerizable sulphonic acids are vinyl sulphonic acid, 4-vinylphenyl sulphonic acid or 3-(methacrylamido)propyl sulphonic acid.

According to the invention compositions are preferred which contain one or more fillers, preferably organic or inorganic particulate fillers. Preferred inorganic particulate fillers are amorphous spherical materials based on oxides, such as $ZrO_2$ and $TiO_2$ or mixed oxides of $SiO_2$, $ZrO_2$, ZnO and/or $TiO_2$, nanoparticulate or micro-fine fillers, such as pyrogenic silica or precipitation silica, as well as minifillers, such as quartz, glass ceramic or glass powder with an average particle size of from 0.01 to 15 μm as well as x-ray-opaque fillers, such as ytterbium trifluoride or nanoparticulate tantalum(V) oxide or barium sulphate or mixed oxides of $SiO_2$ with ytterbium(III) oxide or tantalum(V) oxide.

In particular, if the composition according to the invention is envisaged for use as dental cement or dental composite, it preferably contains 30 to 90 wt.-%, particularly preferably 60 to 90 wt.-% of at least one filler, relative to the total mass of the composition.

Additionally, the compositions according to the invention can, if necessary, contain further additives. The additives are preferably selected from stabilizers, dyes, microbiocidal active ingredients, fluoride-ion-releasing additives, optical brighteners, plasticizers, UV absorbers and mixtures thereof.

The compositions according to the invention are particularly suitable as dental substances, adhesives, coatings, cements, composites or shaped parts, in particular as cements and composites and quite particularly as filling composites.

Compositions for use as cements or composites preferably contain 0.002 to 5 wt.-% photoinitiator mixture,
    9 to 59.8 wt.-% polymerizable binder and
    30 to 90 wt.-% filler, relative in each case to the total mass of the composition.

In a further preferred embodiment, compositions for use as cements or composites contain 0.002 to 5 wt.-% photoinitiator mixture,
    9 to 39.8 wt.-% polymerizable binder and
    60 to 90 wt.-% filler, relative in each case to the total mass of the composition.

Particularly preferred compositions thus contain (a) 0.05 to 1.1 wt.-% (relative to the mass of the polymerizable binder) diacylgermanium compound of Formula (I), preferably diacylgermanium compound of Formula (II), and particularly preferably diacylgermanium compound selected from the group consisting of bis(4-methoxybenzoyl)diethylgermanium, dibenzoyl diethylgermanium and mixtures thereof, (b) 0.1 to 1.1 wt.-% (relative to the mass of the polymerizable binder) α-diketone, (c) 0.1 to 2.1 wt.-% (relative to the mass of the polymerizable binder) amine accelerator, (d) 0 to 2.1 wt.-% (relative to the mass of the polymerizable binder) acyl or bisacyl phosphine oxide, (e) 9 to 59.8 wt.-% (relative to the total mass of the composition) polymerizable binder and (f) 30 to 90 wt.-% (relative to the total mass of the composition) filler.

Naturally, the constituents (a) to (f) of this embodiment can have one of the above-named preferred meanings independently of each other. The composition according to the invention thus preferably contains
- (a) 0.05 to 1.1 wt.-% (relative to the mass of the polymerizable binder) diacylgermanium compound of Formula (II), preferably diacylgermanium compound selected from the group consisting of bis(4-methoxybenzoyl)diethylgermanium, dibenzoyl diethylgermanium and mixtures thereof, particularly preferably bis(4-methoxybenzoyl)diethylgermanium,
- (b) 0.1 to 1.1 wt.-% (relative to the mass of the polymerizable binder) α-diketone selected from the group consisting of camphorquinone, 1-phenylpropane-1,2-dione and mixtures thereof, preferably camphorquinone,
- (c) 0.1 to 2.1 wt.-% (relative to the mass of the polymerizable binder) amine accelerator selected from the group consisting of p-(dimethylamino)benzoic acid ethyl ester, dimethylaminoethyl methacrylate, N,N-dimethylaniline, N,N-dimethyl-p-toluidine, triethanolamine and mixtures thereof, preferably p-(dimethylamino)benzoic acid ethyl ester,
- (d) 0 to 2.1 wt.-% (relative to the mass of the polymerizable binder) acyl or bisacyl phosphine oxide selected from the group consisting of 2,4,6-trimethylbenzoyl diphenylphosphine oxide, bis(2,4,6-trimethylbenzoyl)phenylphosphine oxide and mixtures thereof, preferably bis(2,4,6-trimethylbenzoyl)phenylphosphine oxide,
- (e) 9 to 59.8 wt.-% (relative to the total mass of the composition) polymerizable binder and
- (f) 30 to 90 wt.-% (relative to the total mass of the composition) filler.

In a further preferred embodiment, the composition thus contains
- (a) 0.1 to 0.5 wt.-% (relative to the mass of the polymerizable binder) diacylgermanium compound of Formula (II), preferably diacylgermanium compound selected from the group consisting of bis(4-methoxybenzoyl)diethylgermanium, dibenzoyl diethylgermanium and mixtures thereof, particularly preferably bis(4-methoxybenzoyl)diethylgermanium,
- (b) 0.2 to 0.6 wt.-% (relative to the mass of the polymerizable binder) α-diketone selected from the group consisting of camphorquinone, 1-phenylpropane-1,2-dione and mixtures thereof, preferably camphorquinone,
- (c) 0.3 to 1.5 wt.-% (relative to the mass of the polymerizable binder) amine accelerator selected from the group consisting of p-(dimethylamino)benzoic acid ethyl ester, dimethylaminoethyl methacrylate, N,N-dimethylaniline, N,N-dimethyl-p-toluidine, triethanolamine and mixtures thereof, preferably p-(dimethylamino)benzoic acid ethyl ester,
- (d) 0 to 1.5 wt.-% (relative to the mass of the polymerizable binder) acyl or bisacyl phosphine oxide selected from the group consisting of 2,4,6-trimethylbenzoyl diphenylphosphine oxide, bis(2,4,6-trimethylbenzoyl)phenylphosphine oxide and mixtures thereof, preferably bis(2,4,6-trimethylbenzoyl)phenylphosphine oxide,
- (e) 9 to 39.8 wt.-% (relative to the total mass of the composition) polymerizable binder and
- (f) 60 to 90 wt.-% (relative to the total mass of the composition) filler.

In a further particularly preferred embodiment, the composition thus contains
- (a) 0.2 to 0.5 wt.-% (relative to the mass of the polymerizable binder) diacylgermanium compound of Formula (II), preferably diacylgermanium compound selected from the group consisting of bis(4-methoxybenzoyl)diethylgermanium, dibenzoyl diethylgermanium and mixtures thereof, particularly preferably bis(4-methoxybenzoyl)diethylgermanium,
- (b) 0.2 to 0.5 wt.-% (relative to the mass of the polymerizable binder) α-diketone selected from the group consisting of camphorquinone, 1-phenylpropane-1,2-dione and mixtures thereof, preferably camphorquinone,
- (c) 0.4 to 0.8 wt.-% (relative to the mass of the polymerizable binder) amine accelerator selected from the group consisting of p-(dimethylamino)benzoic acid ethyl ester, dimethylaminoethyl methacrylate, N,N-dimethylaniline, N,N-dimethyl-p-toluidine, triethanolamine and mixtures thereof, preferably p-(dimethylamino)benzoic acid ethyl ester,
- (d) 0.1 to 0.6 wt.-% (relative to the mass of the polymerizable binder) acyl or bisacyl phosphine oxide selected from the group consisting of 2,4,6-trimethylbenzoyl diphenylphosphine oxide, bis(2,4,6-trimethylbenzoyl)phenylphosphine oxide and mixtures thereof, preferably bis(2,4,6-trimethylbenzoyl)phenylphosphine oxide,
- (e) 9 to 39.8 wt.-% (relative to the total mass of the composition) polymerizable binder and
- (f) 60 to 90 wt.-% (relative to the total mass of the composition) filler.

The subject of the invention is also a process for preparing a composite in which a composition according to the invention is prepared and then completely or partially cured.

To initiate curing by radical polymerization, the photoinitiator mixture of the composition is preferably irradiated with light in the wavelength range of from 200 to 750 nm, particularly preferably 200 to 550 nm, further preferably 300 to 550 nm and quite particularly preferably 350 to 500 nm. It is particularly advantageous to use an LED light source with a wavelength in the range of from 380 nm to 750 nm, preferably approximately 380 nm to approximately 490 nm. The curing time is preferably approximately 1 to 20 s.

The invention is explained in more detail below by means of examples.

EXAMPLES

Example 1

Light-Curing Composites Based on a Ternary Initiator Composition

Four composites based, relative to the total mass of the composite, on 70 wt.-% of a silanized Ba—Al-boron silicate glass filler (Schott) with an average particle size of 1.0 μm and 30 wt.-% of a mixture of methacrylate monomers and photoinitiator were prepared using a kneader (Linden). The methacrylate monomer mixture contained, relative to its total weight, 4 wt.-% bis-GMA (Esschem), 75 wt.-% UDMA (Ivoclar Vivadent AG) and 21 wt.-% triethylene glycol dimethacrylate (Esschem). As photoinitiator, a mixture of camphorquinone (CQ) and the amine (4-dimethylamino)-benzoic acid ethyl ester (EMBO) (composite A), the germanium photoinitiator bis-(4-methoxybenzoyl)diethylgermanium (BMBDGe, Ivoclar Vivadent AG) (composites B and C) or a mixture of BMBDGe, CQ and EMBO (composite D) was added to the previous methacrylate mixture, in accordance with Table 1, given below. The amounts of initiator components given in Table 1 relate to the total weight of the mixture of methacrylate monomers and initiator components, but not to the total weight of the composition.

The depth of cure was determined in analogy to ISO standard ISO 4049-2009 ("Dentistry—Polymer-based restorative materials"). For this, a cylindrical hole (h=6 mm, d=4 mm) was filled with composite in a metal mould and covered with a transparent film. The composite was then exposed to light against a white background for 10 s with a dental LED light source (Bluephase 20i, Ivoclar Vivadent AG, 1000 mW/cm$^2$, 385-515 nm). Afterwards, the composite was removed from the metal mould and the non-polymerized content was scraped off from the cured part with a plastic spatula. The thickness of the cured test piece is determined using a calliper rule and given as the depth of cure in Table 1. In order to better represent the differences, the layer thickness was not divided by 2.

TABLE 1

Initiator content in the monomer of the composites and depth of cure

|  | BMBDGe [wt.-%] | CQ [wt.-%] | EMBO [wt.-%] | Depth of cure [mm] |
|---|---|---|---|---|
| A* | — | 0.3 | 0.6 | 4.7 |
| B* | 0.2 | — | | 4.7 |
| C* | 0.4 | — | | 5.1 |
| D | 0.4 | 0.3 | 0.6 | 5.6 |

*Comparison example

The results obtained show a significant increase in the depth of cure of the composites with a ternary photoinitiator composition according to the invention compared with composites based on the pure camphorquinone-amine system or the Ge photoinitiator BMBDGe.

Example 2

Light-Curing Composites Based on an Initiator with 4 Components

Two composites based, relative to the total mass of the respective composite, on 87 wt.-% of a filler mixture, namely 35 wt.-% of a Tetric EvoCeram isofiller (Ivoclar Vivadent AG), 39 wt.-% of a silanized Ba—Al borosilicate glass filler (Schott) with an average particle size of 1.5 µm, 5 wt.-% spherosil (silanized $SiO_2$—$ZrO_2$ mixed oxide with an average particle size of 1.2 µm, Tokoyma Soda) and 8 wt.-% $YbF_3$ (ytterbium trifluoride with an average particle size of 0.2 µm, Auer Remy), and 13 wt.-% of a mixture of methacrylate monomers and photoinitiator, were produced using a kneader (Linden). The mixture of methacrylate monomers and photoinitiator contained, relative to its total weight, 20 wt.-% bis-GMA (Esschem), 39.1 wt.-% UDMA (Ivoclar Vivadent AG), 20 wt.-% 2,2-bis[4-(2-methacryloxypropoxy)phenyl]propane (Ivoclar Vivadent AG) and 20 wt.-% p-cumyl-phenoxyethylene glycol methacrylate (CMP-1E, Kowa Chemical Japan) (composite A). Whereas, according to the following Table 2, a mixture of 0.3 wt.-% camphorquinone (CQ) and 0.6 wt.-% (4-dimethylamino)-benzoic acid ethyl ester (EMBO) was used as photoinitiator in composite A, composite B additionally contained, at the expense of UDMA, 0.4 wt.-% of the germanium photoinitiator BMBDGe (bis-(4-methoxybenzoyl)diethyl germanium) and 0.2 wt.-% of the bisacylphosphine oxide Irgacure 819 (bis(2,4,6-trimethylbenzoyl)phenylphosphine oxide, Ciba) (quantities given are in each case relative to the total mass of the mixture of methacrylate monomers and photoinitiator). The depth of cure was determined as described in Example 1.

TABLE 2

Initiator content in the monomer of the composites and depth of cure

|  | BMBDGe [wt.-%] | Irgacure 819 [wt.-%] | CQ [wt.-%] | EMBO [wt.-%] | Depth of cure [mm] |
|---|---|---|---|---|---|
| A* | — | — | 0.3 | 0.6 | 5.6 |
| B | 0.4 | 0.2 | 0.3 | 0.6 | 7.2 |

*Comparison example

The results show a significant improvement in the depth of cure for a composite according to the invention.

In addition, the double bond conversion as a function of the layer thickness was measured using IR spectroscopy according to F. Rueggeberg (Dent. Mater. 10 (1994) 282-286), and reproduced in Table 3. These results also show a much better curing of composite B according to the invention.

TABLE 3

Double bond conversion (given in mol-%) as a function of the initiator system and the layer thickness of the composite

| | layer thickness | | |
| Composite | 1 mm | 3 mm | 5 mm |
|---|---|---|---|
| A* (CQ/EMBO) | 55.1 | 52.1 | 47.0 |
| B (BMBDGe/Irg 819/CQ/EMBO) | 67.4 | 63.2 | 50.7 |

*Comparison example

Moreover, the Vickers hardness profile of the test piece with a layer thickness of 4 mm was determined according to D. C. Watts et al. (Brit. Dent. J., 1984, 209-215) and shown in Table 4. These results also show a better curing of composite B in terms of depth:

TABLE 4

Vickers hardness (VH, given in N/mm$^2$) and surface hardness of composite test pieces (5 s curing with Bluephase 20i)

| Composite (initiator components) | VH at top | VH at bottom | Surface hardness (%) |
|---|---|---|---|
| A* (CQ/EMBO) | 461 | 370 | 80.3 |
| B (BMBDGe/Irg 819/CQ/EMBO) | 552 | 517 | 93.7 |

*Comparison example

Finally, the change in colour of composites A and B during the curing was investigated, and the corresponding results are shown in Table 5.

TABLE 5

Colour values of composites A and B before and after curing
(5 s with Bluephase 20i)

|  | a-value | b-value |
|---|---|---|
| Composite paste |  |  |
| Composite A* | −2.76 | 22.34 |
| Composite B | −5.18 | 29.95 |
| Composite test piece |  |  |
| Composite A* | −0.72 | 11.33 |
| Composite B | −0.75 | 12.38 |

*Comparison example

The paste of composite B with the initiator composition according to the invention has much higher a- and b-values compared with composite A. However, due to the good bleaching behaviour of the composition according to the invention, the a- and b-values in the cured test piece are substantially lower and there are hardly any differences compared with composite A.

Example 3

Curing of a Composite Using Green Light ($\lambda_{max}$=517 nm) and Subsequent Post-Curing Using Blue Light ($\lambda_{max}$=430 nm)

Two composites of the same monomer and filling composition were produced according to Example 2, wherein a mixture of 0.3 wt.-% CQ and 0.6 wt.-% EMBO was used as photoinitiator in composite A (comparison example) and a mixture of 0.3 wt.-% camphorquinone (CQ), 0.6 wt.-% (4-dimethylamino)-benzoic acid ethyl ester (EMBO) and 0.4 wt.-% of the germanium photoinitiator BMBDGe (bis-(4-methoxybenzoyl)diethylgermanium was used in composite C. In a first series of tests, the composites were first exposed to light with a green LED ($\lambda_{max}$=517 nm) for 2×20 s and then the bending strength and the bending E modulus were determined. In a second series of tests, the exposure to light with the green LED (2×20 s) was followed by an exposure to light with a blue LED ($\lambda_{max}$=430 nm) for the same duration. The results of the mechanical tests are shown in Table 6.

TABLE 6

Mechanical properties of composites A and C after one- and two-stage curing

| Property/composite | Curing with green LED ($\lambda_{max}$ = 517 nm) | Curing with blue LED ($\lambda_{max}$ = 430 nm) |
|---|---|---|
| Bending strength (MPa) |  |  |
| Composite A* | 40.8 ± 10.8 | 114.5 ± 5.3 |
| Composite C | 49.4 ± 6.4 | 121.0 ± 3.8 |
| Bending E modulus (MPa) |  |  |
| Composite A* | 1750 ± 420 | 6930 ± 310 |
| Composite C | 2250 ± 390 | 9590 ± 410 |

*Comparison example

The results show that with a photoinitiator that also contains, in addition to CQ and EMBO, a germanium photoinitiator according to Formula (I), a much better two-stage curing can be realized using two light sources of different wavelength ranges.

The invention claimed is:

1. A composition with at least one polymerizable binder, in which it contains a photoinitiator mixture which contains
   (a) at least one diacylgermanium compound of Formula (I),
   (b) at least one α-diketone,
   (c) at least one accelerator and
   (d) at least one acyl- or bisacylphosphine oxide which is selected from the group consisting of 2,4,6-trimethylbenzoyl diphenylphosphine oxide, bis(2,4,6-trimethylbenzoyl)phenylphosphine oxide and mixtures thereof;

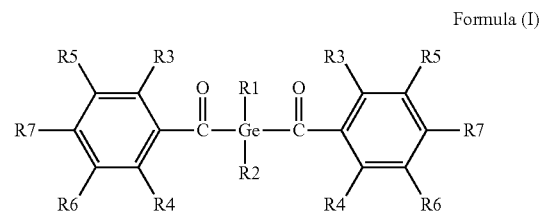

Formula (I)

wherein
   $R^1$, $R^2$ independently of each other are a linear $C_{1-4}$-alkyl, or $C_{2-4}$-alkenyl radical, which can be substituted by one or more polymerizable groups;
   $R^3$, $R^4$ independently of each other are in each case H, halogen, a branched or linear $C_{1-4}$-alkyl or —O—$C_{1-4}$-alkyl radical;
   $R^5$, $R^6$ independently of each other are in each case H, halogen, a linear $C_{1-20}$-alkyl, -alkenyl, -alkoxy or -alkenoxy radical which can be interrupted by one or more —O—, —S— or —NR$^8$-radicals and substituted by one or more polymerizable groups;
   $R^7$ independently of each other is in each case H, halogen, a linear $C_{1-20}$-alkyl, -alkenyl, -alkoxy or -alkenoxy radical which can be interrupted by one or more —O—, —S— or NR$^8$— radicals and substituted by one or more polymerizable groups; and
   $R^8$ independently is in each case H, a $C_{1-20}$-alkyl, -alkenyl, -alkoxy or -alkenoxy radical.

2. A composition according to claim 1, in which the photoinitiator mixture contains, relative to the polymerizable binder
   (a) 0.05 to 1.1 wt.-% o diacylgermanium compound,
   (b) 0.1 to 1.1 wt.-% α-diketone,
   (c) 0.1 to 2.1 wt.-% accelerator and
   (d) 0 to 2.1 wt.-% bisacylphosphine oxide.

3. A composition according to claim 2, in which the photoinitiator mixture contains, relative to the polymerizable binder
   (a) 0.1 to 0.5 wt.-% diacylgermanium compound,
   (b) 0.2 to 0.6 wt.-% α-diketone,
   (c) 0.3 to 1.5 wt.-% accelerator and
   (d) 0 to 1.5 wt.-% acyl- or bisacylphosphine oxide.

4. A composition according to claim 3, in which the photoinitiator mixture contains, relative to the polymerizable binder
   (a) 0.2 to 0.5 wt.-% diacylgermanium compound,
   (b) 0.2 to 0.5 wt.-% α-diketone,
   (c) 0.4 to 0.8 wt.-% accelerator and
   (d) 0.1 to 0.6 wt.-% acyl- or bisacylphosphine oxide.

5. A composition according to claim 1, in which the diacylgermanium compound is a compound of Formula (II)

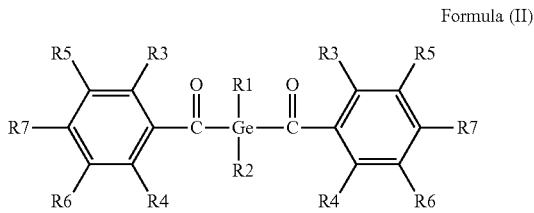

Formula (II)

wherein

R¹, R² independently of each other are a linear $C_{1-4}$-alkyl radical;

R³, R⁴ are in each case H;

R⁵, R⁶ are in each case H; and

R⁷ independently of each other are in each case H, a linear $C_{1-6}$-alkyl or -alkoxy radical.

6. A composition according to claim 5, in which the diacylgermanium compound is selected from the group consisting of bis(4-methoxybenzoyl)diethylgermanium, dibenzoyl diethylgermanium and mixtures thereof.

7. A composition according to claim 1, in which the α-diketone is selected from the group consisting of camphorquinone, 1-phenylpropane-1,2-dione and mixtures thereof.

8. A composition according to claim 1, in which the accelerator is an amine accelerator which is selected from the group consisting of p-(dimethylamino)-benzoic acid ethyl ester, dimethylaminoethyl methacrylate, N,N-dimethylaniline, N,N-dimethyl-p-toluidine, triethanolamine and mixtures thereof.

9. A composition according to claim 1, which contains as polymerizable binder at least one radically polymerizable monomer and/or prepolymer.

10. A composition according to claim 9, which contains as binder a mono- or multifunctional (meth)acrylate, an N-mono- or -disubstituted acrylamide, a bisacrylamide, a radically ring-opening polymerizable monomer, a cyclic allyl sulphide, a polysiloxane based on methacryl silanes or a mixture thereof or a mixture of at least one of the binders with a radically polymerizable, acid-group-containing monomer.

11. A composition according to claim 9, which contains as binder a mono- or multifunctional (meth)acrylate or a mixture thereof.

12. A composition according to claim 1 which additionally contains filler.

13. A composition according to claim 1, which additionally contains at least one additive selected from stabilizers, dyes, microbiocidal active ingredients, fluoride-ion-releasing additives, optical brighteners, plasticizers, UV absorbers and mixtures thereof.

14. A composition according to claim 12, which contains 0.002 to 5 wt.-% photoinitiator mixture, 9 to 59.8 wt.-% polymerizable binder and 30 to 90 wt.-% filler, relative in each case to the total mass of the composition.

15. A process for producing a composite, in which the composition according to claim 1 is produced and then completely or partially cured.

16. The process according to claim 15 producing adhesives, coatings, cements, composites, shaped parts or dental materials.

17. A composition according to claim 1, in which the accelerator is an amine accelerator.

* * * * *